United States Patent [19]

Mahurkar

[11] Patent Number: 4,623,327
[45] Date of Patent: Nov. 18, 1986

[54] METHOD AND APPARATUS FOR USING DUAL-LUMEN CATHETERS FOR EXTRACORPOREAL TREATMENT

[76] Inventor: Sakharam D. Mahurkar, 6171 N. Sheridan, Suite 1112, Chicago, Ill. 60660

[21] Appl. No.: 700,695

[22] Filed: Feb. 12, 1985

[51] Int. Cl.$^4$ ............................................. A61M 1/03
[52] U.S. Cl. ......................................... 604/4; 604/49
[58] Field of Search ........................................ 604/4–6, 604/52, 53, 49; 128/327

[56] References Cited

U.S. PATENT DOCUMENTS

| | | | |
|---|---|---|---|
| D. 250,349 | 11/1978 | McFarlane | D24/54 |
| D. 256,617 | 8/1980 | Clemens | D24/54 |
| D. 272,651 | 2/1984 | Mahurkar . | |
| 998,339 | 7/1911 | Hollins | 27/24 A |
| 1,290,647 | 1/1919 | Nyvall . | |
| 2,175,726 | 10/1939 | Gebauer . | |
| 2,474,665 | 6/1949 | Guarino | 128/DIG. 3 |
| 2,564,977 | 8/1951 | Hsi Hu . | |
| 2,590,895 | 4/1952 | Scarpellino . | |
| 2,625,932 | 1/1953 | Salisbury . | |
| 3,324,853 | 6/1967 | Czorny et al. . | |
| 3,463,152 | 8/1969 | Sorenson . | |
| 3,550,591 | 12/1970 | MacGregor . | |
| 3,804,097 | 4/1974 | Rudie . | |
| 4,027,668 | 6/1977 | Dunn . | |
| 4,096,860 | 6/1978 | McLaughlin . | |
| 4,098,275 | 7/1978 | Consalvo . | |
| 4,099,528 | 7/1978 | Sorenson et al. . | |
| 4,134,402 | 1/1979 | Mahurkar . | |
| 4,144,884 | 3/1979 | Tersteegen et al. . | |
| 4,180,068 | 12/1979 | Jacobsen et al. . | |
| 4,202,332 | 5/1980 | Tersteegen et al. . | |
| 4,203,436 | 5/1980 | Grimsrud . | |
| 4,270,535 | 7/1981 | Bogue et al. . | |
| 4,336,036 | 6/1982 | Leeke et al. . | |
| 4,385,631 | 5/1983 | Uthmann | 604/284 |
| 4,403,983 | 3/1983 | Edelman et al. | 604/43 |
| 4,451,252 | 5/1984 | Martin | 604/43 |
| 4,535,770 | 8/1985 | Lemole | 128/327 |

FOREIGN PATENT DOCUMENTS

| | | |
|---|---|---|
| 834211 | 2/1976 | Belgium . |
| 1092927 | 1/1981 | Canada ................................. 604/43 |
| 50089 | 8/1982 | Canada . |
| 36642 | 9/1981 | European Pat. Off. .............. 604/43 |
| 2259865 | 6/1974 | Fed. Rep. of Germany . |
| MR19346 | 6/1982 | Fed. Rep. of Germany . |
| 592193 | 4/1925 | France . |
| 821344 | 4/1982 | France . |
| 55-88771 | 7/1980 | Japan . |
| 1419702 | 12/1975 | United Kingdom . |
| 1006219 | 3/1983 | United Kingdom . |

OTHER PUBLICATIONS

McIntosh et al., "Double Lumen Catheter," *J.A.M.A.*, Feb. 21, 1959, pp. 137/835–138/836.
*Dorland's Illustrated Medical Dictionary*, 25th Ed., W. B. Saunders Co., Philadelphia, 1974, p. 274.
Brenner & Rector, *The Kidney*, vol. III, W. B. Saunders Co., Philadelphia, 1976, p. 164.
*ASAIO Abstracts*, vol. 5, 22nd Annual Meeting, San Francisco California, Apr. 1–3, 1976, p. 52.

*Primary Examiner*—Stephen C. Pellegrino
*Attorney, Agent, or Firm*—Leydig, Voit & Mayer, Ltd.

[57] ABSTRACT

A patient dependent on extracorporeal treatments is subjected to minimal insertion trauma and pain both before and after a fistula operation. A phlebotomy method is disclosed using a veno-occlusive tourniquet or ligation occluding a venous segment at a location between the inlet and return openings of a dual lumen catheter so that a high blood flow rate can be obtained for an extracorporeal treatment system, thereby lessening or delaying the need for a fistula operation. Registration or alignment of the veno-occlusive tourniquet or ligation is ensured by an attachment to the catheter. Preferably the tourniquet or ligation includes an elastic band threaded to the attachment. If a fistula operation becomes necessary or has been performed, insertion trauma and pain is minimized by using a dual-lumen needle having a tapered distal end portion terminating in a beveled cutting edge. Preferably the needle has an outer tube of swaged stainless steel and an internal divider having a distal end portion matching and engaging with the reduced internal diameter of the tapered distal end portion of the outer tube.

10 Claims, 18 Drawing Figures

METHOD AND APPARATUS FOR USING DUAL-LUMEN CATHETERS FOR EXTRACORPOREAL TREATMENT

FIELD OF THE INVENTION

The present invention relates generally to extracorporeal treatments in which blood and its components are treated outside of the body and which require access to the circulatory system of the human body and, more particularly, to dual-lumen catheters and catheterization methods for use in such treatments. As used herein, the term "catheter" includes rigid metal devices such as needles as well as flexible or semi-rigid polymeric devices.

BACKGROUND OF THE INVENTION

The circulatory access for extracorporeal treatments such as hemodialysis, hemofiltration, plasmapheresis, cytopheresis, and component blood banking, poses special problems. Because of the quantitative nature of the extracorporeal processes, and due to the fact that clearance rates of selected substances from the blood are directly related to the rate at which blood flows to and from the system, high blood flow rates to the system are preferable. To achieve these high flow rates, e.g. in excess of 200 ml. per minute, large veins such as the subclavian or femoral veins are usually accessed by the catheters used to gain circulatory access for these treatments. These large veins are located deep, in close proximity to vital organs such as the heart, lungs, and viscera, and are difficult to puncture and lead to a higher incidence of complications due to the blind techniques that must be used.

In order to obtain high blood flow rates from portions of the circulatory system closer to the surface, various surgical techniques are employed, usually in the arm. The blood supply to the arm begins in the brachial artery which divides into three arteries, i.e., the interosseous, radial and ulnar arteries. Arterial blood flow is under relatively high pressure and has a relatively high velocity. After supplying the oxygen and nutritional needs of the tissues, the blood returns via a large number of veins in the arm, including the basalic and cephalic veins.

Since the blood brought to the arm by three arteries is returned through a multitude of venous channels, each venous channel carries a small fraction of the blood. This blood is under relatively low pressure and moves slowly, and the blood from the central veins cannot flow to the peripheral veins because of the one-way valves in the veins. Therefore, in their natural state the veins are not able to provide adequate blood flow for most extracorporeal treatments. Consequently, the surgical techniques referred to above are used to join one of the arteries in the arm with an adjacent vein, and diverting the arterial blood flow through the vein. Such a vein is known as a "fistula" and can be readily accessed to supply blood to the extracorporeal treatment system.

A fistula is typically accessed by either two single-lumen catheters or a single double-lumen catheter in order to provide simultaneous flow into and out of the vein. The use of single-lumen catheters requiring two needle punctures is yet to be replaced by the use of a single double-lumen catheter requiring a single needle puncture, largely because of a disproportionate increase in pain and trauma resulting from the larger puncture for the double-lumen catheter.

Double-lumen catheters and cannulas have employed both coaxial lumens and lumens adjacent to one another. It is now known, however, that the preferred lumen geometry includes two side-by-side semicircular lumens. Coaxial catheters and cannulas are described, for example, in McLaughlin U.S. Pat. No. 4,096,860; Sorenson et al. U.S. Pat. No. 4,099,528; Tursteegen et al. U.S. Pat. No. 4,202,332; and Udall Canadian Pat. No. 1,092,927. Dual-lumen catheters and cannulas having lumens adjacent to one another are described, for example, in Consalvo U.S. Pat. No. 4,098,275; Mahurkar U.S. Pat. No. 4,134,402; Belan Belgium Pat. No. 8,342,211; Jacobson et al. U.S. Pat. No. 4,180,068; Grimsrud U.S. Pat. No. 4,203,436; Uthmann U.S. Pat. No. 4,385,631; Mahurkar U.S. Design Pat. No. D272,651; Edelman U.S. Pat. No. 4,403,983; and Martin U.S. Pat. No. 4,451,252.

SUMMARY OF THE INVENTION

It is a primary object of the present invention to provide an improved catheterization method and apparatus for concurrently and continuously withdrawing blood from, and returning blood to, unaltered peripheral veins at relatively high blood flow rates (e.g., rates in excess of 100–200 ml/minute), using only a single puncture and without surgical intervention. Thus, a related object of the invention is to provide an improved catheterization method and apparatus which permit dual-lumen catheters to be used in unaltered peripheral veins for extracorporeal treatments requiring relatively high blood flow rates.

A further object of the invention is to provide such an improved catheterization method and apparatus which are relatively simple and economical to use.

A still further object of the invention is to provide an improved dual-lumen needle for accessing the circulatory system with a single puncture and minimal insertion trauma and pain. In this connection, a related object of the invention is to provide such an improved dual-lumen needle which prolongs the life of a fistula.

Still another object of the invention is to provide such an improved dual-lumen needle which significantly reduces the cutting trauma during penetration of the needle, and which permits entry of the needle into the fistula without jeopardizing the blood flow rate and without increasing the pressure.

Yet another object of the invention is to provide an improved method of manufacturing dual-lumen needles for accessing circulatory systems.

Other objects and advantages of the invention will be apparent from the following detailed description and the accompany drawings.

In accordance with an important aspect of the present invention, a dual-lumen catheter is inserted into a venous segment in the direction of the venous blood flow, with a single puncture of the venous segment, the catheter having an intake lumen for withdrawing blood from the venous segment and a return lumen for returning blood to the venous segment; and then the venous segment is occluded so that the segment is engorged on one side of the occlusion and partially collapsed on the other side of the occlusion, the occlusion being positioned in such a way that the entrance to the intake lumen is located in the engorged portion of the venous segment, and the exit from the return lumen is located in the partially collapsed portion of the venous segment.

Another important aspect of the present invention also provides an improved dual-lumen needle comprising an elongated hollow cylinder having a tapered distal end portion to reduce the diameter of the cylinder at that end, the tapered distal end being beveled to form a cutting edge for initiating punctures; a longitudinal septum disposed within the cylinder and dividing the interior of the cylinder into a pair of longitudinal lumens, one of the lumens extending along the full length of the cylinder so that it is open at the beveled distal end, and the other lumen terminating a predetermined distance away from the beveled distal end by merging the septum with the side wall of the cylinder; and at least one aperture formed in the cylinder wall near the end of the terminated lumen to provide access to that lumen through the side wall of the cylinder.

DESCRIPTION OF PREFERRED EMBODIMENTS

Although the invention will be described in connection with certain preferred embodiments, it is to be understood that there is no intention to limit the invention to these particular embodiments; to the contrary, various changes and modifications can be made therein without departing from the spirit and scope of the invention, and it is intended to cover all such changes and modifications that fall within the spirit and scope of the appended claims.

Figures 1, 2:
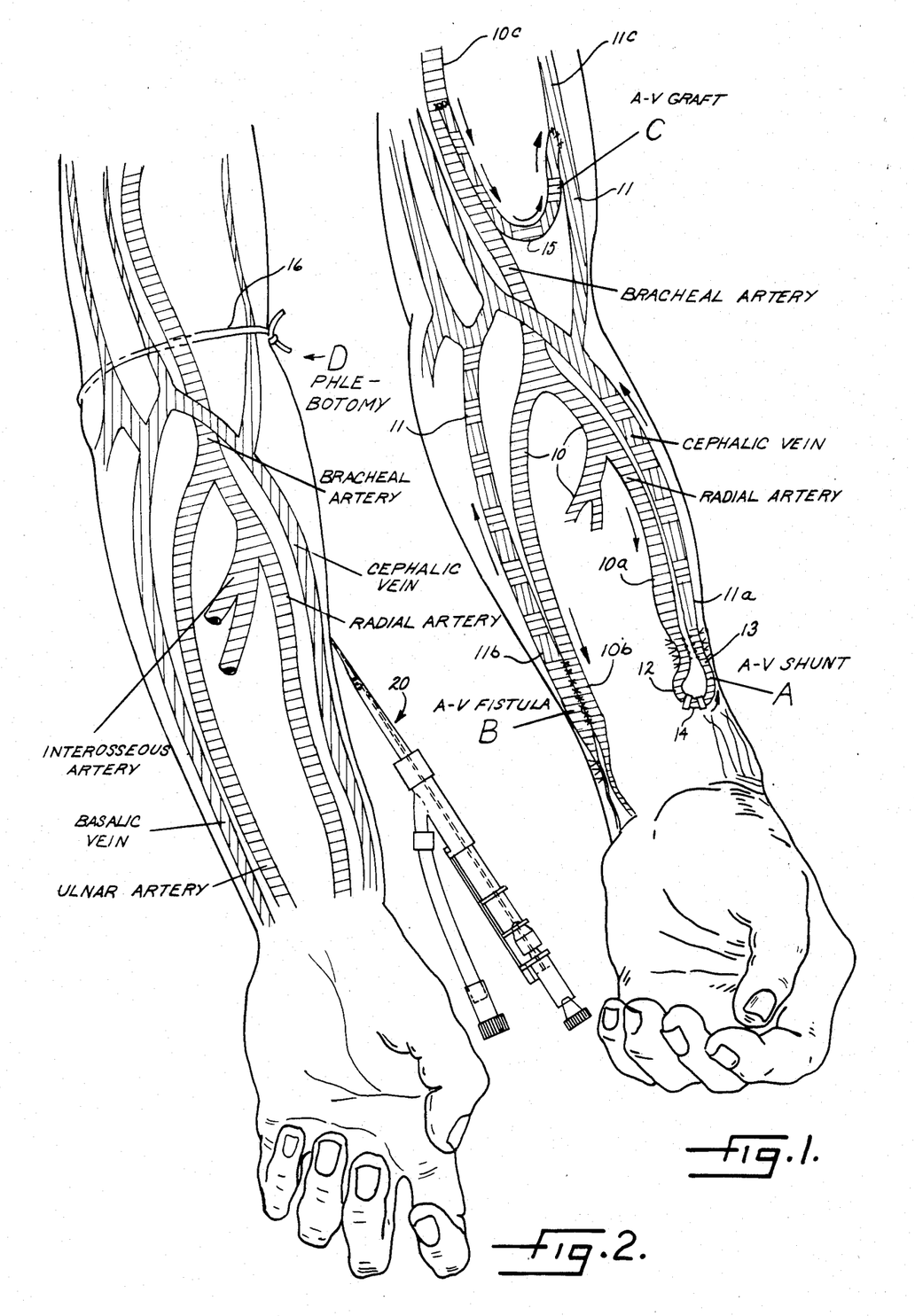
FIG. 1 is a diagrammatic illustration of the anatomy of a portion of the circulatory system of the arm containing various surgical alterations that are made in the arm to augment the blood flow through a vein when the vein is to be accessed for extracorporeal treatment of the blood.
FIG. 2 is a diagrammatic illustration of a portion of the anatomy of the circulatory system of the arm, with a veno-occlusive tourniquet or ligature applied to produce venous engorgement for phlebotomy.

Referring now to the drawings and turning first to FIG. 1, a human arm includes arteries 10 for carrying blood from the heart to the capillaries extending throughout the arm and hand, and a larger number of veins 11 for returning the blood to the heart. As mentioned previously, the arterial blood flow is at a considerably higher pressure and velocity than the venous blood flow, and the arteries are located in deeper parts of the arm than the veins.

In order to obtain adequate blood flow from portions of the circulatory system near the surface, the following surgical procedures, illustrated in FIG. 1, are commonly performed:

A. Shunt: Silastic tubes 12 and 13 are inserted into the ends of an artery 10a and an adjacent vein 11a while the distal ends of the artery and vein are cut off and ligated. The arterial tube 12 provides blood for processing in the extracorporeal equipment, while the venous tube 13 returns the processed blood. The silastic tubes protrude through the skin, and between treatments they are joined by a connector 14 which shunts arterial blood directly into the vein.

B. Fistula: The end or side of an artery 10b is surgically connected to the end of an adjacent vein 11b. This admits the high-pressure, high-velocity arterial blood flow directly into the vein 11b, which in time dilates and can be repeatedly punctured to obtain adequate blood for extracorporeal treatments.

C. Graft: In this procedure a synthetic or biologic tube 15 is surgically interposed between an artery 10c and a vein 11c. The high-pressure, high-velocity blood gushes into the low-resistance venous system via the graft, which can be repeatedly punctured or can have permanent ports for obtaining blood for extracorporeal treatments.

D. Phlebotomy: Venous blood at low flow rates, e.g. 100 ml per minute, can be obtained for transfusions and blood banking via a conventional single-lumen needle (not shown) by impeding the venous return by a veno-occlusive tourniquet such as a pneumatic cuff or ligature 16 (FIG. 2) and pooling the blood. To return the blood to the veins, the occlusion is removed. A single puncture by a convential single-lumen needle (not shown) can be used for intermittent withdrawal and return of the blood by sequentially applying and removing the occlusion. A pneumatic cuff (not shown) is preferred for this purpose since it is easily inflated and deflated to sequentially apply and remove the occlusion. This technique, however, requires complicated equipment and is not suitable for continuous extracorporeal operations utilizing membrane devices and centrifuges. In addition to being intermittent, it produces pressure and velocity oscillations and no-flow states.

Initially shunts made chronic dialysis possible; femoral venipunctures made acute dialysis life-saving; and dual-lumen catheters placed surgically in a femoral vein permitted prolonged acute dialysis treatment. Currently acute dialysis is done via femoral or subclavian venipunctures; chronic dialysis is done via fistulas or grafts; and plasmapheresis or cytopheresis is done via peripheral venipunctures. All the access sites, i.e. the veins, fistulas and grafts, need two punctures, one for withdrawal and another for return of the processed blood. Having two punctures at different sites or in the same vessel is not only painful, but also causes additional trauma to the vessel and shortens the life of the vessel. Single puncture machines with cyclical bidirectional flow require special equipment, are complicated to operate and, as a result, are largely obsolete today. Dual-lumen needles which provide bidirectional flow through a single puncture have been proposed, but have not been adopted because of the penetration hole size, trauma, and accompanying pain.

A dual-lumen catheter 20 for penetrating a vein 11 is shown in detail in FIGS. 3-6. The portion of the catheter 20 which extends into the vein is a polymeric tube 21 having a centrally located longitudinal septum 22 which divides the tube into two longitudinal lumens 23 and 24 of semicircular cross-section (see FIG. 5). The intake lumen 23 is terminated a predetermined distance away from the tip of the catheter and is accessed through a plurality of entrance openings 25. The return lumen 24 extends through the entire length of the tube 21 so that its exit opening 26 is located at the distal end of the catheter. This arrangement permits the externally processed blood to be returned to the vein via the lumen 24 at a point sufficiently far downstream from the entrance openings 25 to ensure that the processed blood returned to the vein is not mixed with the unprocessed blood being withdrawn from the vein.

Figures 3, 4, 5, 6:
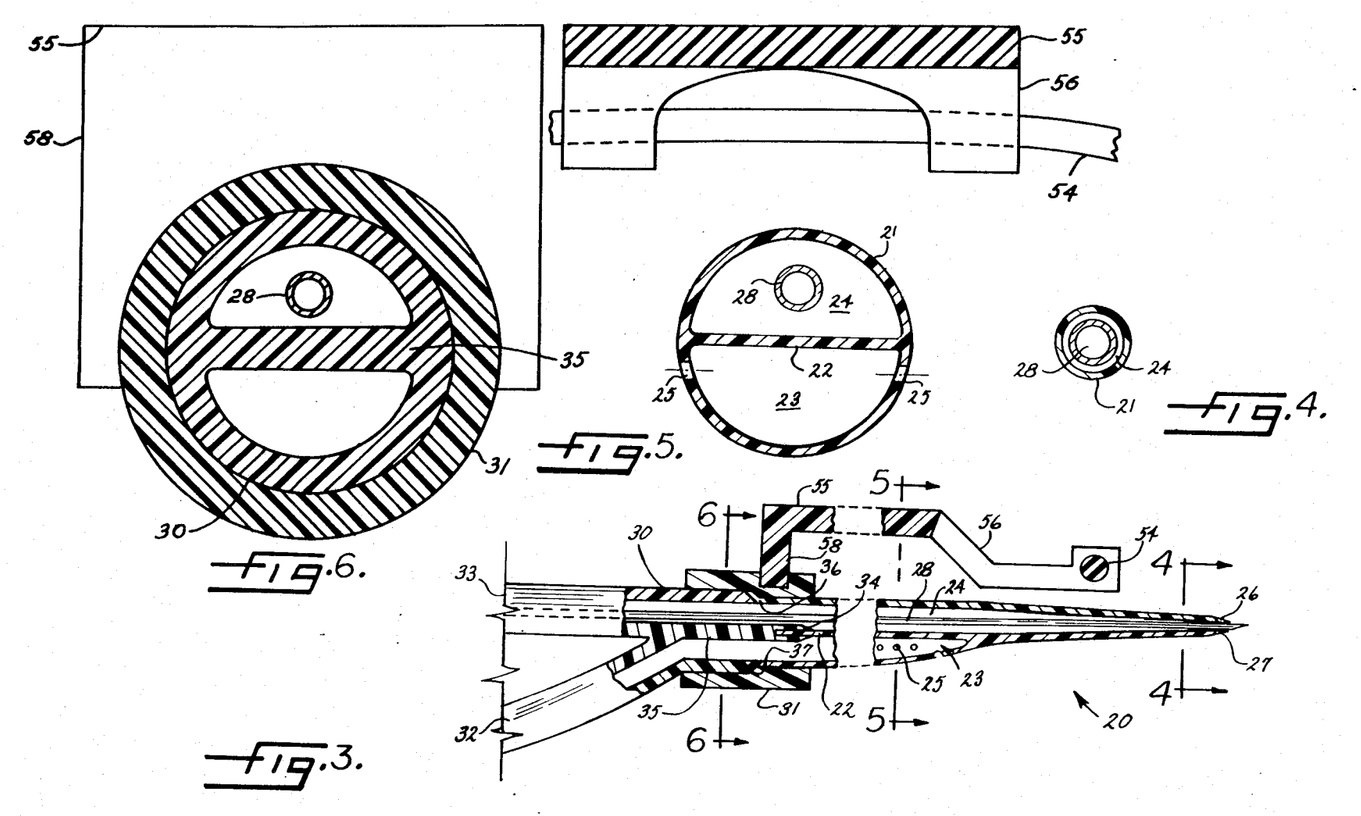
FIG. 3 is a side elevation, partially in section, of a dual-lumen catheter for use in accordance with the present invention.
FIG. 4 is an enlarged section taken generally along line 4—4 in FIG. 3.
FIG. 5 is an enlarged section taken generally along line 5—5 in FIG. 3.
FIG. 6 is an enlarged section taken generally along line 6—6 in FIG. 3.

At the distal end of the catheter 20 the semicircular cross section of the return lumen 24 is gradually converted to a circular cross-section (see FIG. 4) with a beveled tip 27 to facilitate entry through the puncture initiated by a needle 28. As can be seen in FIGS. 3, 4 and 5, the circular cross-section has a much smaller radius than the semicircular cross-section, and is about the same as the radius of the needle 28 so that the catheter tip 27 fits tightly around the needle. The transition from a semicircular to circular cross-section in the return lumen 24 begins about where the intake lumen 23 is terminated. The termination of the intake lumen 23 is effected by merging the semicircular outer wall of the lumen 23 with the central septum 22, as can be seen in FIG. 3. Beyond this merger, the septum becomes part of the circular wall of the return lumen 24.

The semicircular or D-shaped cross-sections of the lumens 23 and 24 permit relatively high flow rates to be achieved in a tube having a relatively small diameter. This configuration is particularly advantageous as compared with, for example, a coaxial pair of lumens. For a given area and pressure difference, the flow in a single direction is only about 15% less in a dual-lumen catheter having semicircular lumens compared to a single lumen catheter, but it is 45% less for a dual-lumen catheter having a coaxial annular lumen.

In order to connect the two lumens 23 and 24 with a pair of flexible tubes 32 and 33 leading to the desired extracorporeal treatment equipment, the catheter 20 is fastened to a Y-shaped connector 30 by means of a surrounding collar 31. More specifically, the central septum 22 of the catheter fits into a slot 34 in a corresponding central divider 35 within the connector 30, and the adjacent outside wall of the catheter 20 is flared outwardly, as at 36 in FIG. 3, to fit against a complementary tapered surface 37 on the end of the connector 30. This outwardly flared portion of the catheter 20 is pressed firmly against the connector surface 37 by the collar 31 which surrounds the adjacent portions of both the catheter 20 and the connector 30. The inside surface of the collar 31 is adhesively bonded to both the catheter 20 and the connector 30. This method of joining the catheter 20 to the Y-shaped connector 30 is especially advantageous since the catheter 20 has a small diameter and its septum 22 and side walls are particularly thin. Therefore, it is relatively difficult to joint the catheter and the Y-shaped connector by the conventional method of inserting the catheter into the Y-shaped connector.

To initiate the puncture through which the catheter 20 is inserted into the desired vein 11, the needle 28 extends through the full length of the return lumen 24 and the mating portion of the connector 30. The end of this needle 28 is fastened to a luer 40 used to telescope the needle through the catheter and into the patient's arm. After the catheter has been inserted into the arm through the puncture initiated by the needle 28, the luer is used to withdraw the needle from the catheter. The return lumen 24 is then clear of any obstructions so that blood can flow smoothly therethrough.

In accordance with an important aspect of the present invention, the venous segment into which the dual-lumen catheter is inserted is occluded between the entrance to the intake lumen and the exit from the return lumen so that the venous segment is engorged on the side of the occlusion where the entrance to the intake lumen is located, and is partially collapsed on the side of the occlusion where the exit from the return lumen is located. With this occlusion, the venous pool of blood in the engorged section of the vein provides a sufficient supply of blood to the intake lumen to permit blood to be withdrawn through that lumen at relatively high flow rates. (The suction to withdraw the blood is provided by the extracorporeal treatment equipment.) At the same time, blood can be returned to the collapsed section of the vein at similarly high flow rates; the flow rate of the returned blood is determined by the pressure produced by the extracorporeal treatment equipment, and the vein will accommodate whatever flow rate is produced by this equipment because the exit of the return lumen is located downstream of the occlusion. That is, the occlusion which produces the venous pool of blood to supply the intake lumen with blood at the desired high flow rate, does not impede the flow of blood through that portion of the vein which receives blood from the return lumen. Consequently, the desired high flow rates can be achieved in both lumens, even though the dual-lumen catheter is inserted in a peripheral vein by a single puncture and without surgical intervention.

With care, a veno-occlusive tourniquet such as a ligature can be manually positioned to occlude the venous segment at a location between the entrance to the intake lumen and the exit from the return lumen of the dual-lumen catheter.

In the particlar embodiment illustrated, however, the proper positioning of the occlusion is facilitated by an occlusion device affixed to the catheter between the entrance to the intake lumen 23 and the exit from the return lumen 24. The preferred embodiment of the occlusion device shown in FIG. 7A and 8–10 comprises an elastic band 50 passed through a pair of apertures in a tension plate 51 mounted on the end of a support arm 52 attached to the catheter collar 31. More particularly, the support arm 52 is rigidly fastened to a semi-cylindrical seating member 52' which is bonded to the outer surface of the collar 31 which holds the catheter in place against the connector 30. The length of the arm 52 is such that the transverse centerline of the tension plate 51, and thus the elastic band 50, is located about midway between the entrance to the intake lumen 23 and the exit from the return lumen 24. Consequently, the occlusion produced by drawing the elastic band 50 taut around the patient's arm will always be located at exactly the desired position relative to the two lumens of the catheter 20.

Figures 7A, 7B, 8, 9, 10:
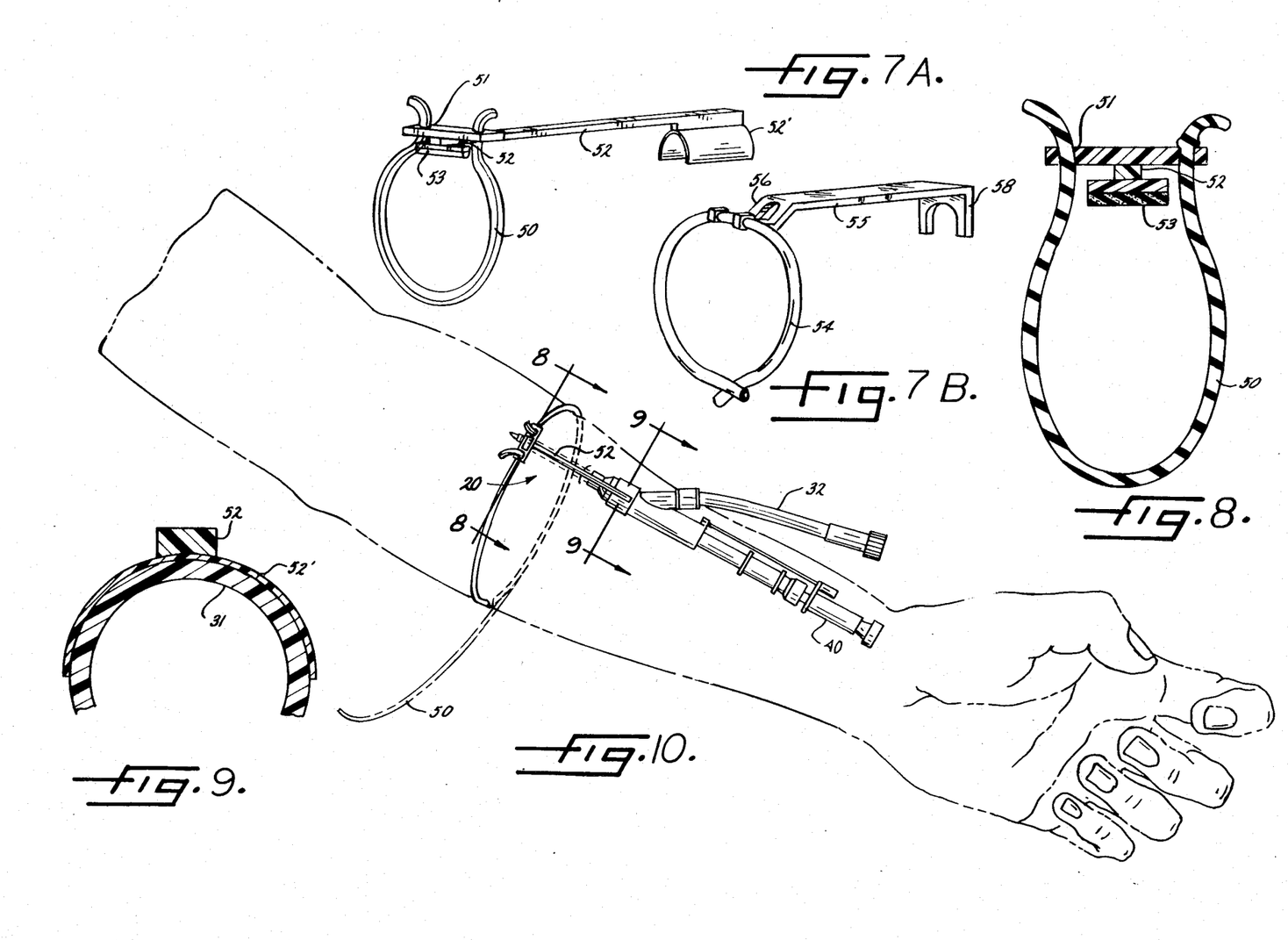
FIG. 7A is a perspective view of a preferred embodiment of a veno-occlusive device attached to the catheter of FIGS. 3–6.
FIG. 7B is a perspective view of a modified embodiment of a veno-occlusive device adapted to be attached to the catheter of FIGS. 3–6.
FIG. 8 is an enlarged section taken generally along the line 8—8 in FIG. 10.
FIG. 9 is an enlarged section taken generally along line 9—9 in FIG. 10.
FIG. 10 is a perspective view of the catheter of FIGS. 3–6 inserted in an arm with the veno-occlusive device of FIG. 7A in its occluding position.

To ensure that the occlusion is continuous around the entire circumference of the arm, a venous compression pad 53 is attached to the underside of the tension plate 51 between the two apertures for the elastic band 50. Thus, when the elastic band 50 is drawn taut, the compression pad 53 is pressed into the portion of the arm which is not engaged by the elastic band. Consequently, the combination of the compression pad 53 and the elastic band 50 provide a substantially continuous occlusion around the entire 360° of the arm circumference.

A modified embodiment of the occlusion device is illustrated in FIG. 7B. In this particular embodiment, the venous compression pad is eliminated because the elastic band 54 is threaded through apertures formed in the enlarged end portions of a pair of fingers 55 and 56 formed as integral parts of a support arm 57. The support arm 57 in turn is mounted on the catheter collar 31 by means of a saddle 58 fitting into a complementary groove formed in the outer surface of the collar. With this modified arrangement the elastic band 54 and the bottom surfaces of the two supporting fingers 55 and 56 form a substantially continuous occlusion around the entire 360° of the arm circumference.

Figure 11:
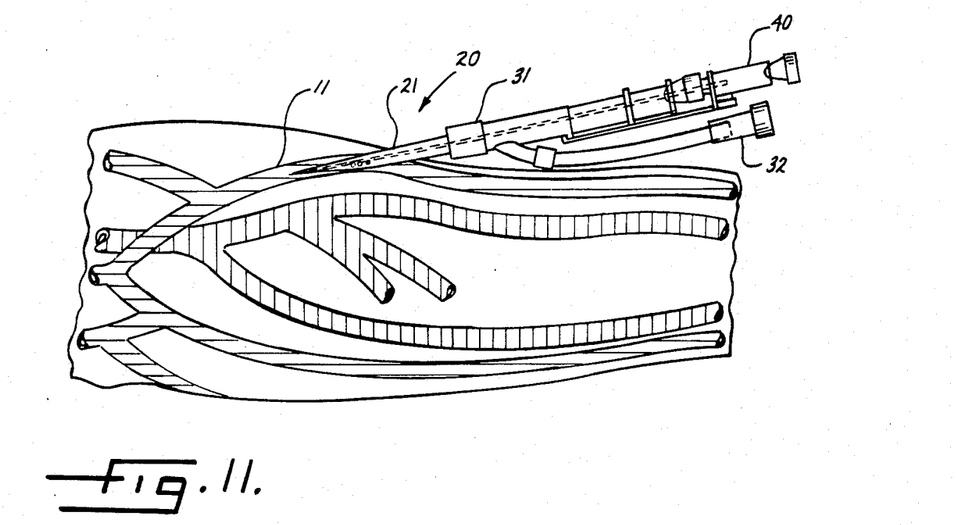
FIG. 11 is a side elevation of the catheter of FIGS. 3–6 initially inserted in a peripheral vein of an arm.
Figure 12:
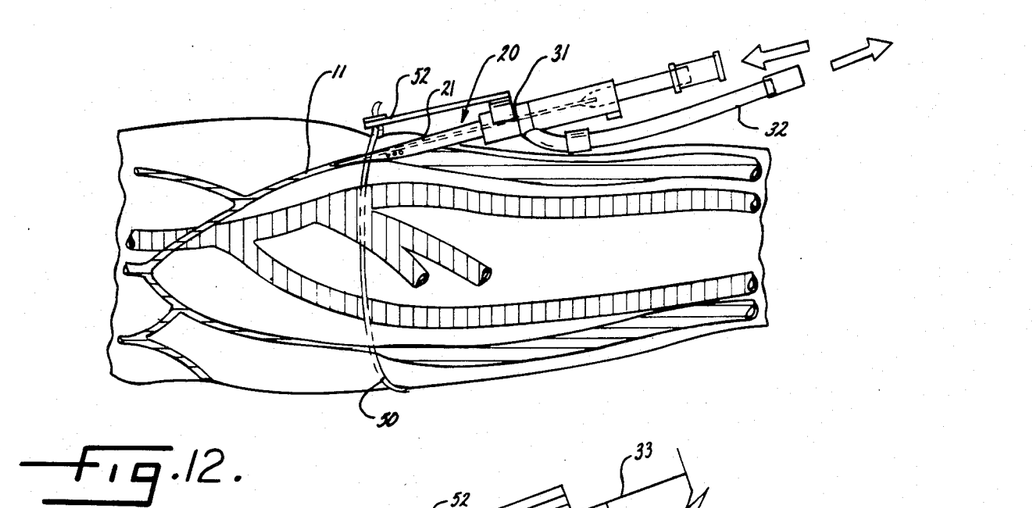
FIG. 12 is a side elevation of the catheter of FIGS. 3–6 inserted in a peripheral vein of an arm and with the veno-occlusive device applied to the arm in its occluding position.
Figure 13:
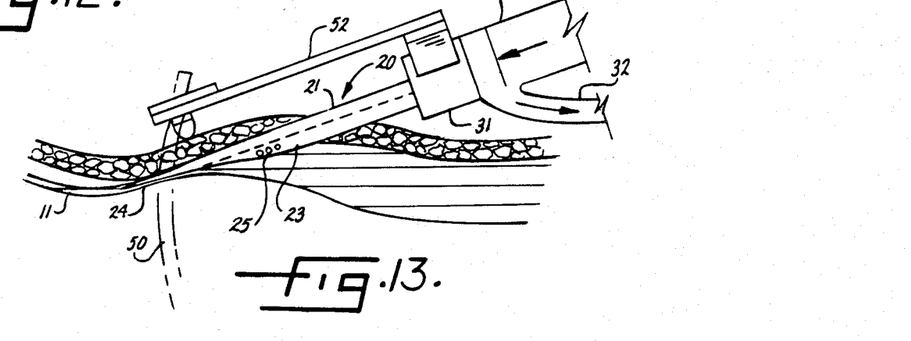
FIG. 13 is an enlarged view of the end portion of the catheter shown in FIG. 12 and the immediately adjacent portion of the vein in which it is inserted.

The method of using a catheter equipped with the venous occlusion device of this invention is illustrated more clearly in FIGS. 11, 12 and 13. In FIG. 11, the tip of the catheter 20 has been inserted into a vein 11; it will be noted that the vein has not yet been occluded. In FIG. 12 the elastic band 50 of the occlusion device has been drawn tightly around the arm, thereby occluding the veins but not the arteries so that proximal to the occlusion the veins become engorged on the intake side of the occlusion. The engorged veins contain a pool of blood and the intercommunication between veins continuously feeds blood to the vein 11 and the intake lumen of the catheter. As further shown in FIG. 13, the occlusion collapses the vein 11 against the distal end portion of the catheter 20 beyond the termination of the intake lumen, so that there is virtually no blood flow through this vein other than that which takes place by way of the intake lumen 23 of the catheter, the extracorporeal treatment system, and the return lumen 24 of the catheter. Because of the engorgement of the vein on the intake side of the occlusion, the blood can be withdrawn from the vein 11 at a relatively high flow rate, and can be returned to the collapsed portion of the vein via the return lumen 24 at substantially the same rate because this portion of the vein is capable of accommodating the large blood flow rate produced by the pressure of the extracorporeal system.

While it is believed that the above-described method is suitable for relatively infrequent use or for a substantial period of time for continuous use, a fistula is generally desirable and may be necessary for frequent and long-term use. In accordance with a further important aspect of the invention, a dual-lumen needle is provided in the form of an elongated hollow cylinder having a tapered distal end portion to reduce the diameter of the cylinder, the distal end being beveled to form a cutting edge for initiating punctures; a longitudinal septum is disposed within the cylinder to divide the interior of the cylinder into a pair of longitudinal lumens, one of the lumens extending along the full length of the cylinder so that it is open at the beveled distal end, the other lumen terminating a predetermined distance away from the beveled distal end by merging the septum with that side of the cylinder wall. At least one aperture is formed in the cylinder wall near the end of the terminated lumen to provide access to that lumen through the side wall of the cylinder. This dual-lumen needle permits high blood flow rates in both directions even though it requires only a single puncture into the fistula. Furthermore, the single puncture causes no more pain or trauma than does a standard dialysis needle which accommodates blood flow in only one direction.

Figure 15:
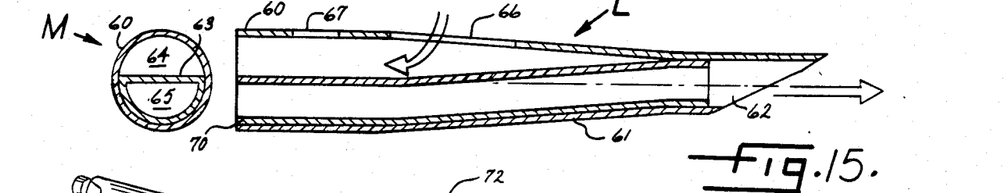
Figure 16:
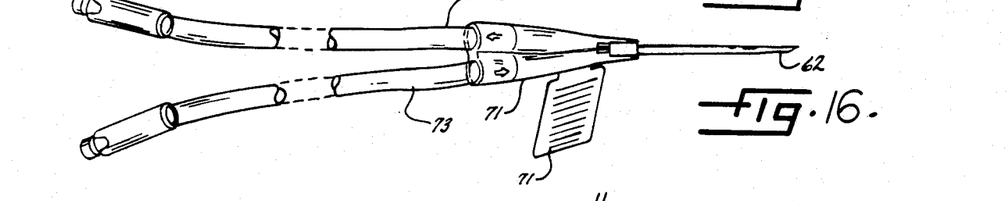
FIG. 16 is a perspective view of the needle of FIG. 15 fastened to a connector and tubes for connection to an extracorporeal treatment system.

In the illustrative embodiment of the dual-lumen needle shown in FIGS. 15 and 16, the needle comprises a thin-walled tube 60, preferably made of 304 stainless steel. The distal end portion of the tube 60 is tapered, as at 61, so as to reduce its diameter, thereby reducing the size of the puncture produced by insertion of the needle into a vein or other vessel. The tapered tip of the tube 60 also has a beveled tip 62 to facilitate the puncture and initial entry of the needle into the body. Due to the geometry of the beveled tip and the taper, the length of the incision is only about 31% of the circumference of the body of the tube.

Inside the tapered tube 60, a centrally located longitudinal septum 63 divides the interior into two longitudinal lumens 64 and 65 of semicircular cross-section. This septum 63 merges with one side of the tube a predetermined distance away from the beveled tip 62, so that the intake lumen 64 terminates at this merger. The return lumen 65 extends through the full length of the tube 60. To provide access to the intake lumen 64, a pair of apertures 66 and 67 are formed in the side wall of the tube. These apertures 66 and 67 are preferably in longitudinal alignment with the longest sidewall of the tube, i.e., with the apex of the beveled end 62. This alignment provides geometrically opposite location of the apertures 66, 67 from the bevel 62 and prevents mixing of processed and unprocessed blood. Since the blood flow is laminar, the intake and return ports merge the blood streams in laminee further apart in the lumen of the fistula and mixing is thereby avoided.

Figure 17:
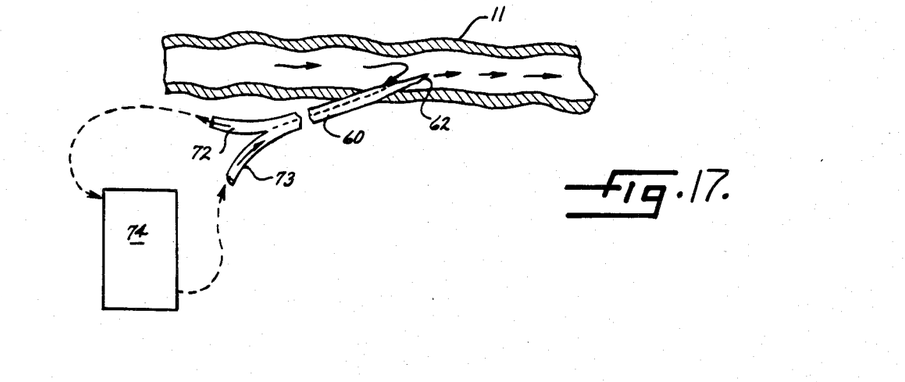
FIG. 17 is a diagrammatic illustration of the needle of FIGS. 15 and 16 inserted into a fistula and supplying blood to an extracorporeal treatment system and returning blood to the fistula from the extracorporeal treatment system.

In use the dual-lumen needle is preferably inserted into the vessel in the direction of blood flow therein, as illustrated in FIG. 17. Because the entrance to the intake lumen 64 and the exit from the return lumen 65 are spaced a substantial distance away from each other, the blood which has been processed by the extracorporeal treatment equipment is not mixed with the unprocessed blood being drawn into the intake lumen.

A preferred method of forming the dual-lumen needle described above is illustrated in FIGS. 14 and 15. This method starts with a thin-walled tube 60 of 304 stainless steel of "half hard" temper. One end of the tube is smoothly tapered by swaging over a hardened internal mandrel so as to reduce both the inside and outside diameters of the tube 60 without increasing the wall thickness, as shown in the cross-sectional side view E and end view F. In fact, the wall thickness is preferably reduced slightly by the swaging operation. Preferably the thin-walled tube 60 is 14 gauge (2.60 mm outside diameter) and is gradually reduced by the taper 61 to 17.5 gauge (1.40 mm outside diameter). By swaging the tube over a hardened internal mandrel, the needle is provided with a smooth internal surface finish which does not promote clotting of blood.

Figure 14:
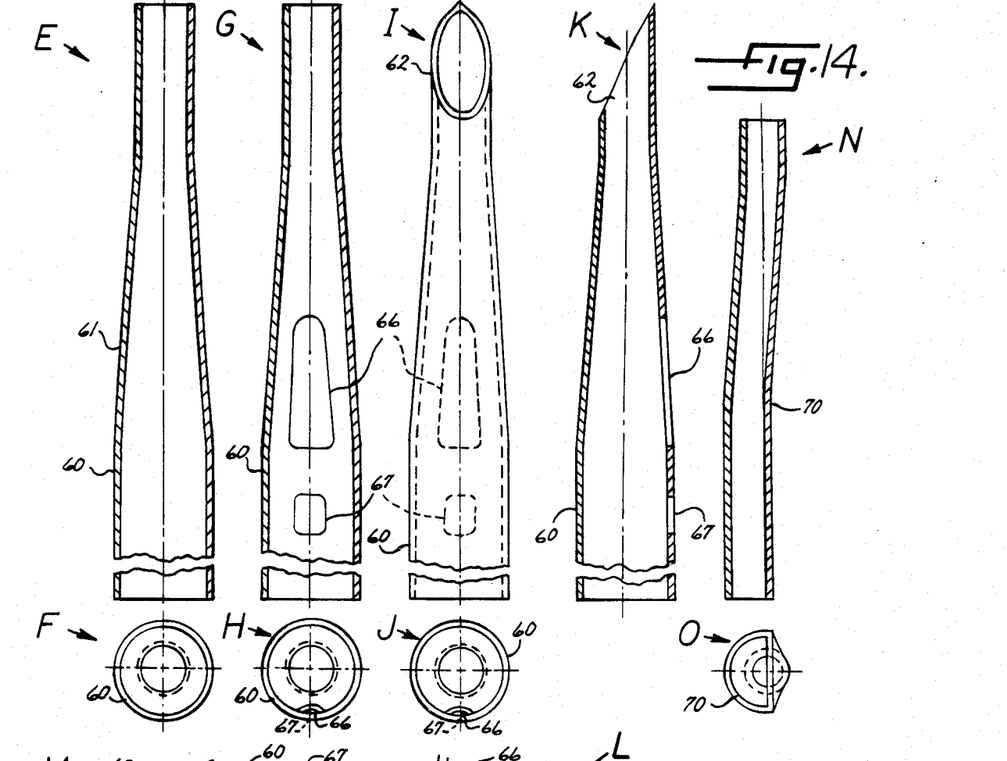
FIGS. 14 and 15 are a sequence of sectional views illustrating the steps involved in forming an improved dual-lumen needle embodying the invention.

Next, the apertures 66 and 67 are provided in the side wall of the tube 60 near the transition or tapered region 61 where the diameter of the tube begins to decrease, as shown in the cross-sectional side view G and end view H. These access openings can be produced by use of a slotting grinding wheel rotating tangent to the tapered surface and moved at right angles to the axis of the tube. As shown in the side view I but not visible in the corresponding end view J, the beveled end 62 on the tapered portion of the tube 60 is produced by a conventional grinding technique using a primary oblique grind with two rotational inclined cuts to obtain a short bevel.

To divide the tapered and beveled tube into two lumens, a semicircular tube 70 is inserted into the tapered and beveled tube to the position illustrated in the cross-sectional view L and corresponding end view M FIG. 15. This semicircular tube 70, shown separately in the cross-sectional view N and end view O of FIG. 14, should have an outside diameter which precisely matches the inside diameter of the distal end portion of the main tube 60, and the wall thickness of the semicircular tube preferably does not exceed about 0.003". As can be seen in FIGS. 14 and 15, the semicircular tube 70 is pre-shaped in the longitudinal direction to exactly match the longitudinally tapered configuration of the main tube 60. It is desirable that the distal end of the partitioning semicircular tube 70 extend into the region between the end of the access aperture 66 and the heel of be beveled tip 62 of the main tube 60. A tight frictional fit of the semicircular partitioning tube 70 within the main tube 60 is generally adequate to hold the needle assembly firmly together, but if desired the inner tube 70 may be adhesively bonded to the inside walls of the main tube 60.

To complete the needle assembly, the metal needle is attached to a Y-shaped connector 71 shown in FIG. 16 which connects the respective lumens 64 and 65 of the needle to a pair of corresponding tubes 72 and 73. Preferably the Y-shaped connector 71 has an integral finger grip 71' for manipulation of the catheter assembly. The finger grip 71' may also be used as a taping surface to anchor the needle during extracorporeal treatment. As further shown in FIG. 17, the tubes 72 and 73 can be connected to the desired extracorporeal treatment system 74 in a conventional manner.

In view of the above, a patient dependent on extracorporeal treatments is subjected to minimal insertion trauma and pain both before and after a fistula operation. By using the phlebotomy method employing a veno-occlusive tourniquet or ligation occluding a venous segment at a location between the inlet and return openings of a dual lumen catheter, a high blood flow rate can be obtained to the extracorporeal treatment system, thereby lessening or delaying the need for a fistula operation. If, however, a fistula operation becomes necessary or has been performed, insertion trauma and pain is minimized by using the above-described dual-lumen needle having a tapered distal end portion terminating in a beveled cutting edge.

What is claimed is:

1. A method of extracorporeal hemodialysis, hemofiltration, plasmapheresis, and cytopheresis treatments of the human blood, requiring continuous blood flow at high glow rates in both directions between the patient and the extracorporeal treatment equipment, in which a catheter having first and second lumens and respective first and second lumen openings axially displaced from each other is inserted into a venous segment so that blood can be withdrawn through one lumen of the catheter and returned through the other lumen, said method comprising the steps of inserting said catheter into said venous segment,
occluding said venous system at a location between said respective first and second lumen openings to engorge the portion of the venous system in which the withdrawal lumen is located, thereby producing a venous pool of blood in the engaged portion of the vein sufficient to permit blood to be withdrawn at relatively high flow rates,
applying a suction to the withdrawal lumen to remove blood from said venous pool at a relatively high rate, and treating the withdrawn blood in extracorporeal treatment equipment, and
returning blood to the non-engorged portion of said venous segment through the return lumen under pressure produced by the extracorporeal treatment equipment.

2. A method as set forth in claim 1 wherein said catheter is inserted into said venous segment in the direction of the venous blood flow.

3. A method as set forth in claim 1 wherein said occlusion is effected with the aid of means mounted on said catheter and positioned to ensure that said venous segment is occlued at said location between said first and second lumen openings.

4. A method as set forth in claim 1 wherein said venous segment is occlued after the insertion of said catheter into said venous segment.

5. A method as set forth in claim 4 wherein external means are mounted on said catheter for aligning a veno-occlusive ligature to occlude said venous segment at said location between said first and second lumen openings, and said step of occluding said venous segment at said location includes the step of applying said veno-occlusive ligature with the aid of said external means.

6. A method as set forth in claim 1 wherein said occlusion is effected by means mounted on said catheter and positioned to ensure that said occlusion is located between the entrance to the intake lumen and the exit from the return lumen.

7. A method as set forth in claim 1 wherein said venous segment is occluded after the insertion of said catheter into said venous segment.

8. A method as set forth in claim 7 wherein external means are mounted on said catheter for aligning a veno-occlusive ligature to occlude said venous segment between the entrance to the intake lumen and the exit from the return lumen, and said step of occluding said venous segment includes the step of applying said veno-occlusive ligature with the aid of said external means.

9. A method of extracorporeal hemodialysis, hemofiltration, plasmapheresis, and cytopheresis treatments of the human blood, requiring continuous blood flow at high flow rates in both directions between the patient and the extracorporeal treatment equipment, in which a dual-lumen catheter is inserted into a venous segment so that blood can be withdrawn through one lumen of the catheter and returned through the other lumen, said method comprising     inserting said dual-lumen catheter into said venous segment in the direction of the venous blood flow, with a single puncture of said venous segment,     occluding said venous system so that said segment is engorged on one side of the occlusion and partially collapsed on the other side of the occlusion, said occlusion being positioned so that the entrance to the intake lumen is located in the engorged portion of the venous segment so that said entrance is located in a venous pool of blood sufficient to permit blood to be withdrawn ar relatively high flow rates, and the exit from the return lumen is located in the partially collapsed portion of the venous segment,     applying a suction to the withdrawal lumen to remove blood from said venous pool at a relatively high rate, and     treating the withdrawn blood in extracorporeal treatment equipment, and returning blood to the non-engorged portion of said venous segment through the return lument under pressure produced by the extracorporeal treatment equipment.

10. A method of extracorporeal hemodialysis, hemofiltration, plasmapheresis, and cytopheresis treatments of the human blood, requiring continuous blood flow at high flow rates in both directions between the patient and the extracorporeal treatment equipment, in which a catheter having first and second lumens and respective first and second lumen openings axially displaced from each other is inserted into a venous segment so that blood can be withdrawn through an intake lumen of the catheter and returned through a return lumen in the same catheter, said method comprising the steps of     inserting said catheter into said venous segment,     occluding the peripheral venous system at a location between said respective first and second lumen openings so that the veins become engorged on the intake side of the occlusion, containing a venous pool of blood which is continuously fed to said intake lumen via the intercommunications among the veins and continuously replenished via the unoccluded arterial blood flow     applying a suction produced by the extracorporeal treatment equipment to the withdrawal lumen to remove blood from said venous pool at a relatively high rate, and treating the withdrawn blood in extracorporeal treatment equipment, and     returning blood to the non-engorged portion of said venous segment through the return lumen under pressure produced by the extracorporeal treatment equipment.

* * * * *